US009463444B2

(12) United States Patent
Xu et al.

(10) Patent No.: US 9,463,444 B2
(45) Date of Patent: Oct. 11, 2016

(54) PREPARATION PROCESS OF NANOCATALYSTS WITH (111) CRYSTAL FACET EXPOSED AND PROCESS FOR VAPOUR-PHASE CO OXIDATIVE COUPLING TO OXALATE

(71) Applicant: Fujian Institute of Research on the Structure of Matter, Chinese Academy of Sciences, Fuzhou, Fujian (CN)

(72) Inventors: Zhongning Xu, Fujian (CN); Guocong Guo, Fujian (CN); Mingsheng Wang, Fujian (CN); Yuangen Yao, Fujian (CN)

(73) Assignee: Fujian Institute of Research on the Structure of Matter, Chinese Academy of Sciences, Fuzhou, Fujian (CN)

( * ) Notice: Subject to any disclaimer, the term of this patent is extended or adjusted under 35 U.S.C. 154(b) by 106 days.

(21) Appl. No.: 14/300,976

(22) Filed: Jun. 10, 2014

(65) Prior Publication Data

US 2014/0296564 A1     Oct. 2, 2014

Related U.S. Application Data

(63) Continuation of application No. PCT/CN2011/083910, filed on Dec. 14, 2011.

(51) Int. Cl.
| | |
|---|---|
| *C07C 67/36* | (2006.01) |
| *B01J 21/04* | (2006.01) |
| *B01J 35/00* | (2006.01) |
| *B01J 23/89* | (2006.01) |
| *B01J 23/44* | (2006.01) |
| *B01J 23/52* | (2006.01) |
| *B01J 23/58* | (2006.01) |
| *B01J 23/60* | (2006.01) |
| *B01J 37/03* | (2006.01) |
| *B01J 37/02* | (2006.01) |

(52) U.S. Cl.
CPC ............. *B01J 23/8953* (2013.01); *B01J 21/04* (2013.01); *B01J 23/44* (2013.01); *B01J 23/52* (2013.01); *B01J 23/58* (2013.01); *B01J 23/60* (2013.01); *B01J 23/892* (2013.01); *B01J 23/8913* (2013.01); *B01J 23/8926* (2013.01); *B01J 23/8946* (2013.01); *B01J 35/002* (2013.01); *B01J 35/006* (2013.01); *B01J 35/0013* (2013.01); *C07C 67/36* (2013.01); *B01J 37/0201* (2013.01); *B01J 37/035* (2013.01)

(58) Field of Classification Search
CPC ....... C07C 67/36; B01J 21/04; B01J 35/002; B01J 35/006
See application file for complete search history.

(56) References Cited

U.S. PATENT DOCUMENTS

| | | | | |
|---|---|---|---|---|
| 4,792,620 A | * | 12/1988 | Paulik | ................. B01J 31/0231 560/232 |
| 2003/0232721 A1 | * | 12/2003 | Zhou | ....................... B01J 23/40 502/325 |

FOREIGN PATENT DOCUMENTS

| | | |
|---|---|---|
| CN | 1148589 A | 4/1997 |
| CN | 1381310 A | 11/2002 |
| CN | 101138722 A | 3/2008 |
| CN | 101279257 A | 10/2008 |
| CN | 101543884 A | 9/2009 |
| CN | 101596455 A | 12/2009 |
| CN | 101612580 A | 12/2009 |
| CN | 101653731 A | 2/2010 |
| CN | 102205242 A | 10/2011 |
| CN | 102513101 A | 6/2012 |
| CN | 102527377 A | 7/2012 |
| WO | 03/064037 A1 | 8/2003 |

OTHER PUBLICATIONS

Kemal et al, Journal of Physical Chemistry C, Experiment and Theoretical Study of Poly(vinyl pyrrolidone)-controlled Gold Nanoparticles, 2008, 112, pp. 15656-15664.*
International Search Report, mailed Sep. 20, 2012, for International Application No. PCT/CN2011/083910, 3 pages.

* cited by examiner

*Primary Examiner* — Paul A Zucker
(74) *Attorney, Agent, or Firm* — Seed IP Law Group PLLC

(57) ABSTRACT

The invention belongs to the technical field of preparing oxalate in coal to ethylene glycol, aiming at providing a preparation process for nanocatalysts with (111) crystal facet exposed and a process for vapor-phase CO oxidative coupling to oxalate. The nanocatalysts with (111) crystal facet exposed comprise carrier, active component and promoter on the carrier, wherein, in term of the weight of the carrier, the active component accounts for 0.05-2% of the weight of the carrier, the weight percentage of metal elements in the promoter is 20% or less. The nanocatalysts with (111) crystal facet exposed are prepared by the nanometals in situ supporting process. The preparation process is simple in procedure, has low energy consumption and can precisely control the size and exposed crystal facet of the active component nanoparticles. The obtained nanocatalysts with (111) crystal facet exposed are highly active for vapor-phase CO oxidative coupling to oxalate at a lower loading of noble metal.

16 Claims, 3 Drawing Sheets

PREPARATION PROCESS OF NANOCATALYSTS WITH (111) CRYSTAL FACET EXPOSED AND PROCESS FOR VAPOUR-PHASE CO OXIDATIVE COUPLING TO OXALATE

CROSS REFERENCE TO RELATED APPLICATIONS

This application is a Continuation Application of International Application No. PCT/CN2011/083910, filed Dec. 14, 2011, which is incorporated herein by reference in its entirety.

TECHNICAL FIELD

The application relates to the synthesis of oxalate in coal to ethylene glycol, especially to a preparation process of nanocatalysts with (111) crystal facet exposed and a preparation process for vapour-phase CO oxidative coupling to oxalate.

BACKGROUND

The coal to ethylene glycol technology mainly includes three steps: a first step, catalytically elimination small amount of hydrogen gas in CO separated by pressure swing adsorption from coal-derived syngas; a second step, vapour-phase CO oxidative coupling to oxalate; and a third step, hydrogenation of oxalate to ethylene glycol. Among them, vapour-phase CO oxidative coupling to oxalate is the key step to realize the conversion of inorganic CO to organic chemical oxalate in coal to ethylene glycol. Oxalates are important organic chemical materials useful for preparing ethylene glycol, oxalic acid, oxalyl chloride, oxalic amide, some medicaments, dyes, and intermediates of the solvents. Currently, oxalates are produced by the process of esterifying dehydration from oxalic acid and alcohol employing toluene or benzene as the dehydrator. This production process has a high process cost, a large energy consumption, serious pollution, and unreasonable material utilization. In 1960s, American, Fenton reported a method for producing oxalates from CO and alcohol by direct coupling, opening a new synthesis routine of oxalates by C1 chemistry. However, this reaction needs to be carried out under the condition of high pressure. Patent JP 8242.656 published patent disclosure reports a process for synthesizing dimethyl oxalate from CO and methyl nitrite under normal pressure employing supported Pd catalyst. The process has good economic efficiency, mild reaction conditions, low energy consumption, no discharge of waste gas, waste liquid and waste solid, and good product quality. The space-time yield of catalyst reported by this patent is 432 $g \cdot L^{-1} \cdot h^{-1}$, which does not decrease after 480 hours of continuous reaction. However, the amount of the noble metal used is large, resulting in a high cost of the catalyst, and the space-time yield is low. After that, lots of patents subsequently report adding promoters such as Zr (CN95116136.9), Ce (CN02111624.5), Ti (CN200710061392.2), La (CN200810114383.X), Ir (CN200810035248.6), Ni (CN200910307543.7), Cu (CN200910060087.0), $MO_x$ (CN200910061854.X), and the like in the catalyst to improve the space-time yield of oxalate. After adding promoter, the space-time yield of oxalate increased to a certain degree, but the amount of the active component Pd is still relatively high. Currently, the actual loading amount of Pd in the industrial plant is about 2%. In addition, all the catalysts reported in the patents and literatures are produced by traditional wet impregnation process, involving steps of immersing, drying, calcinating, reducing at high temperature, and the like. It takes long duration time and high energy consumption. Moreover, it is impossible to conduct the exact control to the size and exposed crystal facet of the Pd particles. However, the size and exposed crystal facet of the Pd particles are two very important parameters influencing the catalytic activity. Therefore, it is especially economically valuable to develop a simple and fast process for producing nanocatalysts with low noble metal loading amount, controllable size and exposed crystal facet as well as high activity for vapour-phase CO oxidative coupling to oxalate.

CONTENTS OF INVENTION

An object of the invention is to provide a nanometals in situ supporting process for preparing nanocatalysts with (111) crystal facet exposed. Comparing with the traditional wet impregnation process in the prior art, this preparation process is simple and fast, the energy consumption is low, and the size and exposed crystal facet of the active component nanoparticles can be exactly controlled.

The nanocatalysts with (111) crystal facet exposed of the invention comprise carrier, active component and promoter on the carrier, wherein, in term of the weight of the carrier, the active component accounts for 0.05-2%, preferably 0.1-1% of the weight of the carrier, and the weight percentage of metal elements in the promoter is 20% or less, preferably 1-10%.

The carrier is one or more selected from α-alumina, magnesia, zinc oxide, silica, zirconia, titania, metal organic frame compounds, active carbon, molecular sieve, carbon nanotube, and graphene, preferably α-alumina, magnesia, or zinc oxide.

The active component is any one metal or a mixture of two or more metals, or an alloy of two or more metals selected from palladium, platinum, and gold, preferably palladium.

The morphology of the active component is non-spherical polyhedron, where the exposed crystal facet of the non-spherical polyhedron is mainly (111) facet, specifically, 50% or more of the exposed crystal facet of the non-spherical polyhedron is (111) facet.

The average particle size of the active component is 1-25 nm, preferably in a range of 2-10 nm, further preferably in a range of 2-3 nm.

The promoter is any one metal or a mixture of two or more metals selected from iron, cobalt, nickel and copper; or any one or two or more selected from iron oxides, cobalt oxides, nickel oxide and copper oxides.

The nanometals in situ supporting process for preparing the nanocatalysts with (111) crystal facet exposed of the invention comprises the following steps:

step a), adding carrier into a mixed solution of active component precursor, reductant, capping agent, and stabilizer;

step b), in situ supporting the active component nanoparticles onto the carrier under the condition of heating and stirring;

step c), washing and drying the sample obtained in step b), to obtain the nanocatalysts with (111) crystal facet exposed.

As a preferred embodiment, it comprises the following steps:

step a) placing the carrier in a solution containing promoter metal salt, mixing uniformly, under the presence of ultrasonic wave, removing the solvent, drying at 100-200° C. for 1-20 hours, calcinating at 200-600° C. for 1-20 hours;

step b) adding the sample obtained in step a) into a mixed solution of active component precursor, reductant, capping agent, and stabilizer;

step c) in situ supporting the resulted active component nanoparticles onto the carrier under the condition of heating and stirring;

step d) washing the sample obtained in step c) with acetone, water and ethanol for three times, then drying in vacuum for 1-20 hours, to obtain the nanocatalysts with (111) crystal facet exposed.

The promoter metal salt in the preparation process is the precursor of promoter, and is one compound or the combination of two or more compounds selected from nitrate, acetate, and halide of iron, cobalt, nickel and copper.

The active component precursor in the preparation process is one compound or the combination of two or more compounds selected from nitrate, acetate, and halide.

The reductant in the preparation process comprises, but not limits to, one compound or the combination of two or more compounds selected from sodium borohydride, hydrazine hydrate, ascorbic acid, formaldehyde, formic acid, sodium formate, sodium acetate, citric acid, glucose, and ethylene glycol. The amount of the reductant used is 1-10 times of that of the active component precursor. The function of the reductant is for reducing the cations of the active component in the precursor to zero-valent metal nanoparticles. The selection of the reductants with different strengths can control the reducing velocity, so as to control the growth speed of the nanocrystals.

The capping agent is selected from compounds containing a citrate or oxalate ion, of which the amount is 1-10 times of that of the active component precursor. The function of the capping agent is for controlling the growth speeds of different crystal facets, so as to controllably synthesize nanoparticles with different crystal facets exposed. Citrate or oxalate ion can selectively cover the (111) crystal facet of the active component, suppressing the growth of (111) crystal facet of the active component, so as to expose (after the capping agent is removed) the (111) crystal facet of the finally synthesized active component. The purpose of capping agent can be achieved as long as the anion part comprises a citrate or oxalate ion, regardless that the compound is an acid or a salt, and the cation is an inorganic ion or an organic ion. If the capping agent is changed to a halogen ion, Pd nanocubes with (100) crystal facet exposed is then obtained. The activity of such Pd nanocubes for vapour-phase CO oxidative coupling to oxalate is much lower than that of Pd non-spherical polyhedron with (111) crystal facet mainly exposed (see Table 2 for the comparison of the catalytic performances data), which shows that the exposed (111) crystal facet of Pd is the active crystal facet for vapour-phase CO oxidative coupling to oxalate.

The stabilizer is selected from organic polymers, such as polyvinylpyrrolidone (PVP) or poly(ethylene oxide)-poly(propylene oxide)-poly(ethylene oxide) triblock copolymer (P123), and the like, or a long chain alkylammonium salt, such as cetyl trimethyl ammonium bromide (CTAB) or cetyl trimethyl ammonium chloride (CTAC), and the like, of which the amount is 1-100 times of the active component precursor. The function of the stabilizer is for suppressing the aggregation of nanoparticles.

As a preferred embodiment, the mass ratio of active component precursor:reductant:capping agent:stabilizer is 1:1-10:1-10:2-40. A person skilled in the art may select a proper condition in the above range according to the practical requirements of the production.

The heating temperature in the preparation process is in the range of 50-200° C., preferably in the range of 80-150° C., and further preferably in the range of 90-110° C.

The heating time in the preparation process is in the range of 0.1-24 hours, preferably in the range of 0.5-5 hours.

The frequency of the ultrasonic wave used in the preparation process is 20 KHz or more, preferably the frequency is 20-200 KHz. A person skilled in the art can select a proper frequency of the ultrasonic wave according to the general knowledge.

Another object of the invention is to provide a process for vapour-phase CO oxidative coupling to oxalate, characterized in that a feed gas containing CO (20-40%), nitrite (10-30%), and nitrogen gas (30-70%), in volume percentage, is passed through a reactor loaded with nanocatalysts with (111) crystal facet exposed to produce oxalate by vapour-phase oxidative coupling reaction, in the reaction conditions with a space velocity of 500-5000 $h^{-1}$, a temperature of 90-160° C. and a pressure of 0.01-2 MPa.

The nanocatalysts with (111) crystal facet exposed in the process for vapour-phase CO oxidative coupling to oxalate is produced by employing the nanometals in situ supporting process of the invention.

Nitrite in the process for vapour-phase CO oxidative coupling to oxalate is any one of methyl nitrite and ethyl nitrite.

The oxalate in the process for vapour-phase CO oxidative coupling to oxalate is any one selected from dimethyl oxalate or diethyl oxalate.

The reactor in process for vapour-phase CO oxidative coupling to oxalate is any one of a single-tubular fixed bed reactor and a multitubular fixed bed reactor.

The advantageous effect of the invention:

1. The morphology, the exposed crystal facet, and the particle size of the active component nanoparticles can be suitably controlled by the nanometals in situ supporting process of the present invention.

2. The nanocatalysts with (111) crystal facet exposed prepared by the nanometals in situ supporting process of the present invention are highly active for vapour-phase CO oxidative coupling to oxalate at a lower loading of noble metal, and the conversion of CO, the selectivity for oxalate, and space-time yield thereof are all relative high.

3. The process for preparing nanocatalysts has short duration, low energy consumption, and is advantageous for industrialisation.

SPECIFIC EMBODIMENTS

The present invention is further described in combination with the following specific Examples and Comparative Examples, but the invention is not limited to the following Examples.

The instruments used in characterization and evaluation of the catalyst:

Transmission electron microscope, high resolution transmission electron microscope: JEOL Ltd., JEM-2010, 200 kV; inductively coupled plasma emission spectroscopy: HORIBA Jobin Yvon, Ultima2, France; micro catalyst evaluation device: Beijing Weikendu Technology Co., Ltd., custom-made; gas chromatography: Shimadzu, GC-2014.

Illustration concerting the lattice spacing, the gas phase space velocity, and the space-time yield:

Lattice spacing refers to the space between two lattice fringes in the high resolution transmission electron micrograph of the Pd nanocrystals. In the face centered cubic Pd nanocrystals, the lattice spacing of (111) crystal facet is 0.226 nm, and the lattice spacing of (200) crystal facet is 0.197 nm. Therefore, if the lattice spacing equals to or closes to 0.226 nm, it indicates that the exposed crystal facet of the Pd nanocrystals is (111) facet. The gas phase space velocity means the volume of reactants passing through unit volume of catalyst per unit time (unit: $h^{-1}$). The space-time yield means under the specified reaction condition, the amount of a certain product obtained in unit time by unit volume (or weight) of catalyst (unit: $g \cdot L^{-1} \cdot h^{-1}$). It is the measure of the activity of catalyst and one of the indications of the productivity of the reactor device.

EXAMPLES

Example 1

1 g of α-alumina was weighed and added into 20 mL of aqueous solution containing 0.010 g of Pd(OAc)$_2$, 0.016 g of ascorbic acid, 0.054 g of sodium oxalate, and 0.111 g of polyvinylpyrrolidone (PVP), and then was mixed at 100° C. for 0.5 hours, washed with acetone, water, and ethanol for three times, and finally dried in vacuum at 60° C. for 2 hours. The transmission electron micrograph of the obtained sample was shown in FIG. 1. As seen from the figure, Pd nanoparticles were uniformly dispersed on the surface of the carrier, and particles appeared as non-spherical polyhedrons with an average size of 2-3 nm. The high resolution transmission electron micrographs of this sample were shown in FIGS. 5 to 8. As seen from the figures, the lattice spacing of the non-spherical polyhedron particles was 0.226 nm, which consisted with the lattice spacing of Pd face centered cubic (111) crystal facet. Thereby, its exposed crystal facet was (111) facet. The statistics of the analysis results of multiple high resolution transmission electron micrographs showed that, 50% or more of the exposed crystal facet of such non-spherical polyhedron was (111) facet. The actual loading amount of Pd measured by inductively coupled plasma emission spectroscopy was 0.37%.

Evaluation of the catalyst: The nanocatalyst of Example 1 was applied to the reaction of vapour-phase CO oxidative coupling to oxalate. The used amount of nanocatalyst was 1 mL. In the source gases, N$_2$:CO:RONO=48:28:20 (volume ratio). The gas phase space velocity was 3000 $h^{-1}$. The reaction temperature was 90-160° C. The reaction pressure was 0.1 MPa. The raw materials and products were monitored and analyzed on line by gas chromatography. Reaction results were shown in Table 1.

TABLE 1 catalytic performances of the nanocatalyst of Example 1 in the reaction of vapour-phase CO oxidative coupling to oxalate

| Reaction temperature (° C.) | One pass conversion of CO (%) | Selectivity for oxalate (%) | Space-time yield of oxalate ($g \cdot L^{-1} \cdot h^{-1}$) |
|---|---|---|---|
| 90  | 1  | 95  | 31 |
| 100 | 8  | 99  | 170 |
| 110 | 20 | 100 | 438 |
| 120 | 33 | 100 | 727 |
| 130 | 41 | 99  | 910 |
| 140 | 46 | 99  | 1006 |
| 150 | 48 | 97  | 1034 |
| 160 | 49 | 99  | 1072 |

Comparative Example 1

Figure 2:
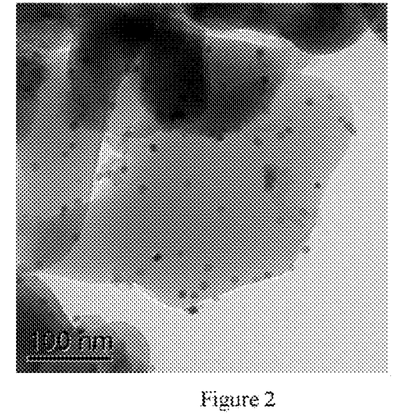
FIG. 2 is the transmission electron micrograph of 0.93% Pd/α-$Al_2O_3$ nanocatalyst prepared in Comparative Example 1.
Figure 9:
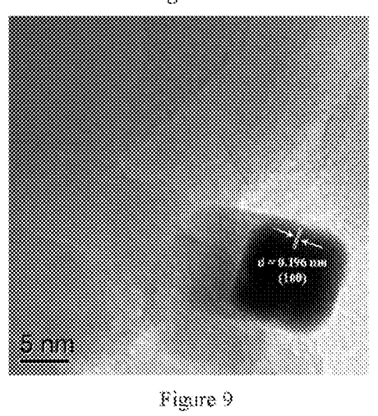
FIG. 9 and FIG. 10 are the high resolution transmission electron micrographs of 0.93% Pd/α-$Al_2O_3$ nanocatalyst prepared in Comparative Example 1.
Figure 10:
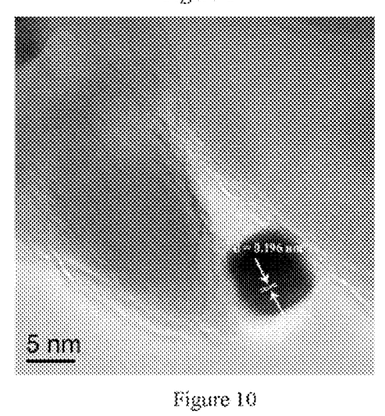
Figure 11:
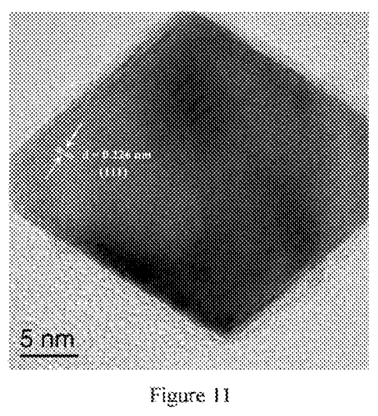
FIGS. 11 to 14 are the high resolution transmission electron micrographs of 0.39% Pd/α-$Al_2O_3$ nanocatalyst prepared in Example 2.
Figure 12:
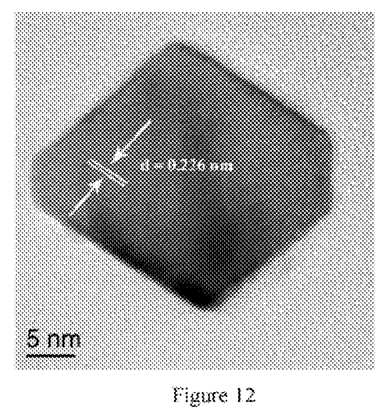
Figure 13:
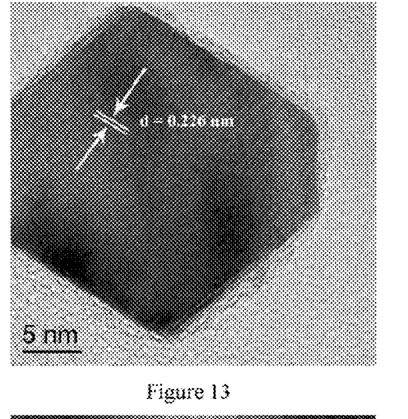
Figure 14:
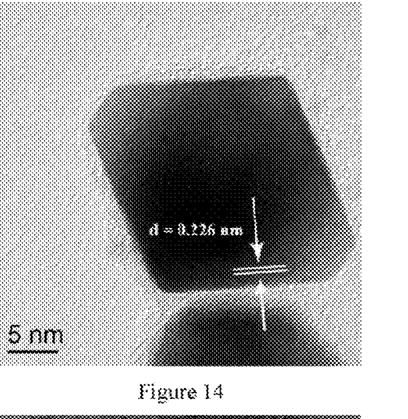
Figure 15:
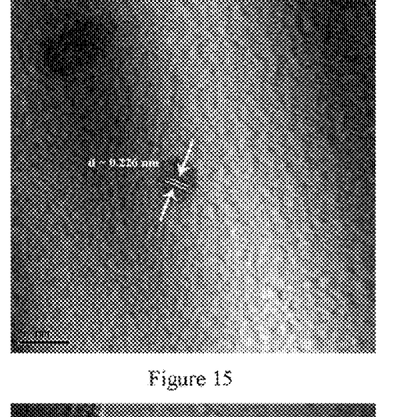
FIGS. 15 to 18 are the high resolution transmission electron micrographs of 0.2% Pd/α-$Al_2O_3$ nanocatalyst prepared in Example 3.
Figure 16:
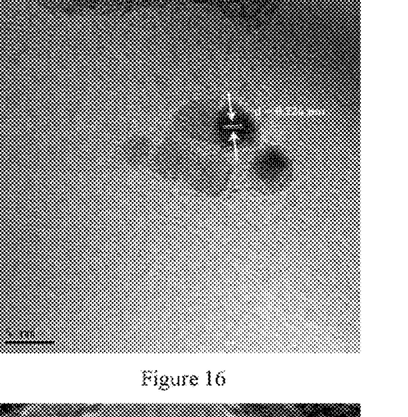
Figure 17:
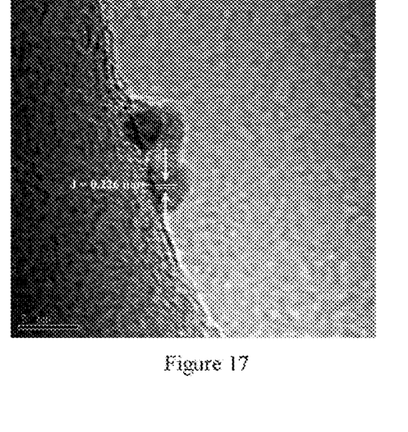
Figure 18:
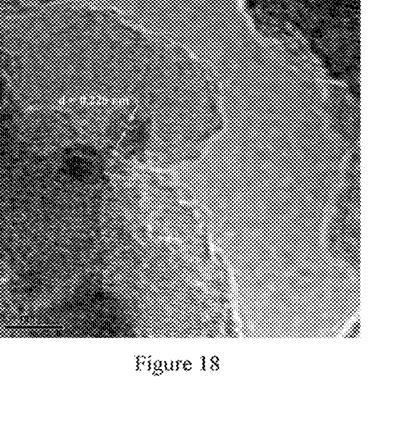

1 g of α-alumina was weighed and added into 20 mL of aqueous solution containing 0.018 g of K$_2$PdCl$_6$, 0.009 g of PdCl$_2$, 0.035 g of ascorbic acid, 0.179 g of KBr, and 0.222 g of polyvinylpyrrolidone (PVP), and then was mixed at 100° C. for 0.5 hours, washed with acetone, water, and ethanol for three times, and finally dried in vacuum at 60° C. for 2 hours. The transmission electron micrograph of the obtained sample was shown in FIG. 2. As seen from the figure, Pd nanoparticles were uniformly dispersed on the surface of the carrier, and particles were all cubes with an average size of 9-10 nm. The high resolution transmission electron micrographs of this sample were shown in FIG. 9 and FIG. 10. As seen from the figures, the lattice spacing thereof was 0.196 nm, which consisted with the lattice spacing of Pd face centered cubic (200) facet. Thereby, its exposed crystal facet was (100) facet. The actual loading amount of Pd measured by inductively coupled plasma emission spectroscopy was 0.93%.

The nanocatalyst of Comparative Example 1 was evaluated in the same manner as that in Example 1, wherein the reaction temperature was 130° C. Reaction results were shown in Table 2.

TABLE 2

Influence of Pd exposed crystal facets on catalytic performances

| | Pd exposed crystal facet | One pass conversion of CO (%) | Selectivity for oxalate (%) | Space-time yield of oxalates ($g \cdot L^{-1} \cdot h^{-1}$) |
|---|---|---|---|---|
| Example 1 | (111) | 41 | 99 | 910 |
| Comparative Example 1 | (100) | 10 | 88 | 187 |

As seen from the data in Table 2, the catalytic performances of the Pd nanoparticles with (111) crystal facet exposed are much higher than the Pd nanocubes with (100) crystal facet exposed, indicating that the Pd (111) facet is the active crystal facet for vapour-phase CO oxidative coupling to oxalate, and the preparation process of the invention can synthesize non-spherical polyhedrons with (111) crystal facet mainly exposed in a controllable manner.

Example 2

1 g of α-alumina was weighed and added into 20 mL of aqueous solution containing 0.015 g of K$_2$PdCl$_4$, 0.084 g of citric acid, and 0.111 g of polyvinylpyrrolidone (PVP). Upon it was heated to 60° C., 1 mL of formaldehyde was added, mixed for 3 hours, washed with acetone, water, and ethanol for three times, and dried in vacuum at 60° C. for 2 hours.

Figure 3:
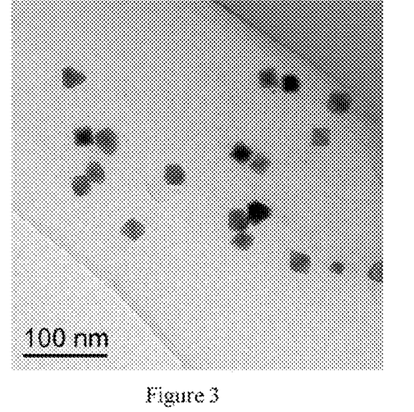
FIG. 3 is the transmission electron micrograph of the 0.39% Pd/α-$Al_2O_3$ nanocatalyst prepared in Example 2.

The transmission electron micrograph was shown in FIG. 3. As seen from the figure, Pd nanoparticles were highly dispersed on the surface of the carrier, and particles were represented as octahedron, with an average size of 20-22 nm. The high resolution transmission electron micrographs were shown in FIGS. 11 to 14. As seen from the figures, the lattice spacing of octahedron particles was 0.226 nm, which consisted with the lattice spacing of Pd face centered cubic (111) facet, i.e. the exposed crystal facet thereof was (111) facet. The statistics of the analysis results of multiple high resolution transmission electron micrographs showed that, 50% or more of the exposed crystal facet of such octahedron was (111) facet. The actual loading amount of Pd measured by inductively coupled plasma emission spectroscopy was 0.39%.

Example 3

Figure 4:
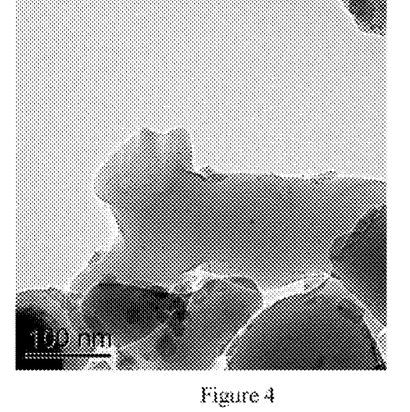
FIG. 4 is the transmission electron micrograph of the 0.2% Pd/α-$Al_2O_3$ nanocatalyst prepared in Example 3.
Figure 5:
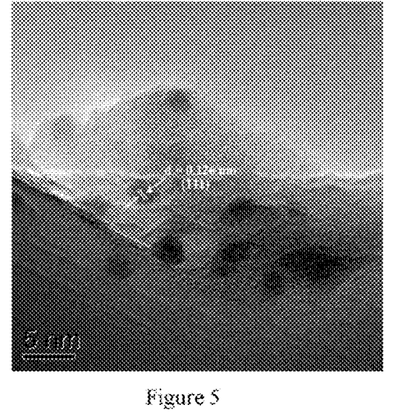
FIGS. 5 to 8 are the high resolution transmission electron micrographs of 0.37% Pd/α-$Al_2O_3$ nanocatalyst prepared in Example 1.
Figure 6:
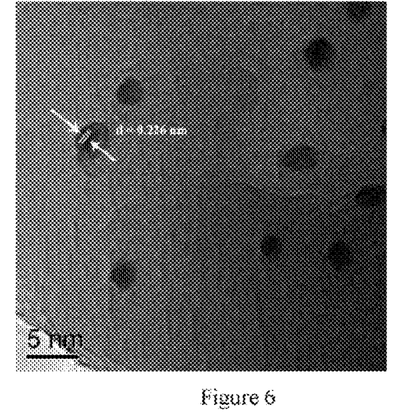
Figure 7:
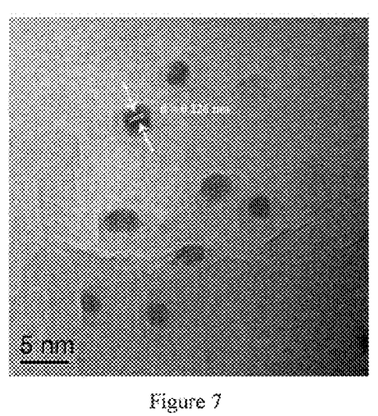
Figure 8:
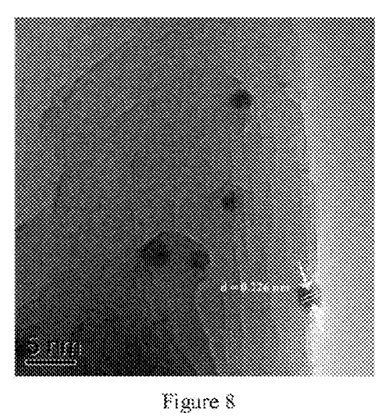

1 g of α-alumina was weighed and added into 20 mL of aqueous solution containing 0.004 g of $Pd(OAc)_2$, 0.007 g of sodium formate, 0.084 g of citric acid, and 0.111 g of polyvinylpyrrolidone (PVP), and then was mixed at 100° C. for 0.5 hours, washed with acetone, water, and ethanol for three times, and dried in vacuum at 60° C. for 2 hours. The transmission electron micrograph was shown in FIG. 4. As seen from the figure, Pd nanoparticles were highly dispersed on the surface of the carrier, and particles were represented as non-spherical polyhedron, with an average size of 2-3 nm. The high resolution transmission electron micrographs were shown in FIGS. 15 to 18. As seen from the figures, the lattice spacing of non-spherical polyhedron particles was 0.226 nm, which consisted with the lattice spacing of Pd face centered cubic (111) facet, i.e. the exposed crystal facet was (111) facet. The statistics of the analysis results of multiple high resolution transmission electron micrographs showed that, 50% or more of the exposed crystal facet of such non-spherical polyhedron was (111) facet.

Example 4

Except for the amount of $Pd(OAc)_2$ as Pd precursor was 0.020 g, the other steps were the same as Example 3.

Example 5

Except for the amount of $Pd(OAc)_2$ as Pd precursor was 0.040 g, the other steps were the same as Example 3.

The nanocatalysts of Example 2-5 were evaluated in the same manner as that of Example 1, wherein the reaction temperature was 130° C. Reaction results were shown in Table 3.

TABLE 3

| | Pd loading amount | Pd particles size (nm) | One pass conversion of CO (%) | Selectivity for oxalate (%) | Space-time yield of oxalate ($g \cdot L^{-1} \cdot h^{-1}$) |
|---|---|---|---|---|---|
| Example 1 | 0.37% | 2-3 | 41 | 99 | 910 |
| Example 2 | 0.39% | 20-22 | 32 | 91 | 642 |
| Example 3 | 0.2% | 2-3 | 26 | 99 | 575 |
| Example 4 | 1% | 2-3 | 40 | 93 | 824 |
| Example 5 | 2% | 2-3 | 42 | 92 | 862 |

Figure 1:
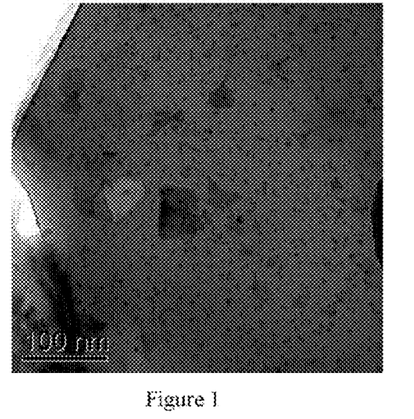
FIG. 1 is the transmission electron micrograph of 0.37% Pd/α-$Al_2O_3$ nanocatalyst prepared in Example 1.

As seen from the data of Table 3, high activities can also be achieved under low loading amount of catalyst. It shows that the Pd nanoparticles in the Pd nanocatalysts of the invention are highly dispersed on the surface of the carrier without aggregation, which can also be proven by the transmission electron micrograph obtained in Example 1.

Example 6

Except for the amount of $K_2PdCl_4$ as Pd precursor was 0.015 g, the other steps were the same as Example 1.

Example 7

Except for the amount of $Pd(NO_3)_2$ as Pd precursor was 0.010 g, the other steps were the same as Example 1.

As seen from the transmission electron micrograph and high resolution transmission electron micrograph, nanocatalysts of Examples 6 and 7 functioned similarly as Example 1. Furthermore, the nanocatalysts of Examples 6 and 7 were evaluated in the same manner as Example 1, wherein the reaction temperature was 130° C. Reaction results were shown in Table 4.

TABLE 4

Influence of different Pd precursors on catalytic performances

| | Pd precursor | One pass conversion of CO (%) | Selectivity for oxalate (%) | Space-time yield of oxalate ($g \cdot L^{-1} \cdot h^{-1}$) |
|---|---|---|---|---|
| Example 1 | $Pd(OAc)_2$ | 41 | 99 | 910 |
| Example 6 | $K_2PdCl_4$ | 40 | 93 | 824 |
| Example 7 | $Pd(NO_3)_2$ | 42 | 92 | 862 |

As seen from the data in Table 4, the type of Pd precursor has little influence on the catalytic performances, and the performances of the nanocatalysts obtained from three precursors are very similar with each other.

Comparative Example 2

Except for replacing α-alumina to γ-alumina, the other steps were the same as Example 1.

The influences of carriers on catalytic performances were shown in Table 5. The reaction temperature was 130° C.

TABLE 5

Influence of carriers on catalytic performances

| | Carrier | One pass conversion of CO (%) | Selectivity for oxalate (%) | Space-time yield of oxalate ($g \cdot L^{-1} \cdot h^{-1}$) |
|---|---|---|---|---|
| Example 1 | α-alumina | 41 | 99 | 910 |
| Comparative Example 2 | γ-alumina | 0 | 0 | 0 |

As seen from the data in Table 5, when γ-alumina carrier was employed, there is no activity. However, when α-alumina carrier was employed, the activity was very high. It shows that α-alumina is effective carrier useful for vapour-phase CO oxidative coupling to oxalate.

Examples 8-14

1 g of carrier was weighed and added into aqueous solution containing active component precursor, reductant, capping agent, and stabilizer as shown in Table 6. The reaction was conducted at 90° C. for 1 hour. The product was washed with acetone, water, and ethanol for three times, dried in vacuum at 60° C. for 2 hours, obtaining nanocatalysts of Examples 8-14. The number of Examples and specific conditions for the preparation are shown in Table 6.

TABLE 6

Conditions for preparation of nanocatalysts of Examples 8-14

| Number of Example | Carrier | Type of the active component precursor | Amount of the active component element | Types and adding amounts of the reductant, capping agent, and stabilizer |
|---|---|---|---|---|
| 8 | Magnesia | Pd(OAc)$_2$ | Pd: 0.005 g | sodium borohydride 0.01 g, citric acid 0.05 g, polyvinylpyrrolidone 0.2 g |
| 9 | Zinc oxide | K$_2$PtCl$_4$ | Pt: 0.005 g | hydrazine hydrate 0.01 g, oxalic acid 0.05 g, poly(ethylene oxide)-poly(propylene oxide)-poly(ethylene oxide) triblock copolymer 0.2 g |
| 10 | Silica | HAuCl$_4$ | Au: 0.005 g | formaldehyde 1 mL, sodium citrate 0.05 g, polyvinylpyrrolidone 0.2 g |
| 11 | Zirconia | K$_2$PdCl$_4$ and K$_2$PtCl$_4$ | Pd: 0.0025 g Pt: 0.0025 g | (sodium formate 0.02 g + sodium acetate 0.02 g), sodium oxalate 0.05 g, cetyl trimethyl ammonium bromide 0.2 g |
| 12 | Titania | K$_2$PdCl$_4$ and HAuCl$_4$ | Pd: 0.0025 g Au: 0.0025 g | glucose 0.05 g, citric acid 0.05 g, polyvinylpyrrolidone 0.2 g |
| 13 | Active carbon | Pd(NO$_3$)$_2$ | Pd: 0.005 g | ethylene glycol 0.05 g, oxalic acid 0.05 g, poly(ethylene oxide)-poly(propylene oxide)-poly(ethylene oxide) triblock copolymer 0.2 g |
| 14 | Graphene | Pd(OAc)$_2$ | Pd: 0.005 g | ascorbic acid 0.04 g, citric acid 0.05 g, polyvinylpyrrolidone 0.2 g |

Examples 15-21

1 g of carrier was weighed and added into a solution containing promoter metal salt, and uniformly mixed. After removing the solvent in the presence of ultrasonic wave, drying at 120° C. for 10 hours, and calcinating at 400° C. for 4 hours, the obtained sample was added to an aqueous solution containing active component precursor, reductant, capping agent, and stabilizer as shown in Table 7. The reaction was conducted at 100° C. for 1 hour. The product was washed with acetone, water, and ethanol for three times, dried in vacuum at 60° C. for 2 hours, obtaining nanocatalysts of Examples 15-21. The number of Examples and specific conditions for the preparation were shown in Table 7.

TABLE 7

Conditions for preparation of nanocatalysts of Examples 15-21

| Number of Example | Carrier | Promoter metal salt | | Active component precursor | | Types and adding amounts of the reductant, capping agent, and stabilizer |
|---|---|---|---|---|---|---|
| | | Type of the promoter metal salt | Mass of the metal element | Type of the active component precursor | Mass of the active component element | |
| 15 | Magnesia | FeCl$_3$ | Fe: 0.05 g | Pd(OAc)$_2$ | Pd: 0.005 g | sodium borohydride 0.01 g, citric acid 0.05 g, polyvinylpyrrolidone 0.2 g |
| 16 | Zinc oxide | CoCl$_2$•6H$_2$O | Co: 0.05 g | K$_2$PtCl$_4$ | Pt: 0.005 g | hydrazine hydrate 0.01 g, oxalic acid 0.05 g, poly(ethylene oxide)-poly(propylene oxide)-poly(ethylene oxide) triblock copolymer 0.2 g |
| 17 | Silica | CuCl$_2$•2H$_2$O and Ni(NO$_3$)$_2$•6H$_2$O | Cu: 0.03 g Ni: 0.03 g | HAuCl$_4$ | Au: 0.005 g | formaldehyde 1 mL, sodium citrate 0.05 g, polyvinylpyrrolidone 0.2 g |
| 18 | Zirconia | CoCl$_2$•6H$_2$O | Co: 0.05 g | K$_2$PdCl$_4$ and K$_2$PtCl$_4$ | Pd: 0.0025 g Pt: 0.0025 g | (sodium formate 0.02 g + sodium acetate 0.02 g), sodium oxalate 0.05 g, cetyl trimethyl ammonium bromide 0.2 g |
| 19 | Titania | Ni(NO$_3$)$_2$•6H$_2$O | Ni: 0.05 g | K$_2$PdCl$_4$ and HAuCl$_4$ | Pd: 0.0025 g Au: 0.0025 g | glucose 0.05 g, citric acid 0.05 g, polyvinylpyrrolidone 0.2 g |

TABLE 7-continued

Conditions for preparation of nanocatalysts of Examples 15-21

| Number of Example | Carrier | Promoter metal salt | | Active component precursor | | Types and adding amounts of the reductant, capping agent, and stabilizer |
|---|---|---|---|---|---|---|
| | | Type of the promoter metal salt | Mass of the metal element | Type of the active component precursor | Mass of the active component element | |
| 20 | Active carbon | $CuCl_2 \cdot 2H_2O$ and $CoCl_2 \cdot 6H_2O$ | Cu: 0.03 g Co: 0.03 g | $Pd(NO_3)_2$ | Pd: 0.005 g | ethylene glycol 0.05 g, oxalic acid 0.05 g, poly(ethylene oxide)-poly(propylene oxide)-poly(ethylene oxide) oxide triblock copolymer 0.2 g |
| 21 | Graphene | $CuCl_2 \cdot 2H_2O$ and $Ni(NO_3)_2 \cdot 6H_2O$ | Cu: 0.03 g Ni: 0.03 g | $Pd(OAc)_2$ | Pd: 0.005 g | ascorbic acid 0.04 g, citric acid 0.05 g, polyvinylpyrrolidone 0.2 g |

The nanocatalysts of Examples 8-21 were evaluated in the same manner as Example 1, wherein the reaction temperature was 130° C. Reaction results were shown in Table 8.

TABLE 8 catalytic performances of nanocatalysts of Examples 8-21 in the reaction of vapour-phase CO oxidative coupling to oxalate

| | One pass conversion of CO (%) | Selectivity for oxalate (%) | Space-time yield of oxalate $(g \cdot L^{-1} \cdot h^{-1})$ |
|---|---|---|---|
| Example 8 | 36 | 97 | 773 |
| Example 9 | 30 | 95 | 631 |
| Example 10 | 26 | 90 | 518 |
| Example 11 | 44 | 99 | 964 |
| Example 12 | 38 | 95 | 799 |
| Example 13 | 30 | 97 | 644 |
| Example 14 | 42 | 98 | 911 |
| Example 15 | 38 | 97 | 816 |
| Example 16 | 32 | 96 | 680 |
| Example 17 | 34 | 93 | 700 |
| Example 18 | 47 | 99 | 1030 |
| Example 19 | 40 | 95 | 841 |
| Example 20 | 32 | 97 | 687 |
| Example 21 | 44 | 99 | 964 |

Comparative Example 3

0.5% Pd/α-alumina catalyst was prepared according to the process disclosed by WO03064037A, in the following steps of 1. weighing 0.01 g of palladium acetate and 0.05 g of glycolic acid and dissolving them in 10 mL of water, and mixing for 1 hour;
2. feeding nitrogen gas and hydrogen gas into the solution to conduct the reduction;
3. weighing 1 g of α-alumina carrier and immersing in the mixed solution after the reduction;
4. drying immersed carrier; and
5. reducing the dried immersed carrier by hydrogen gas at 300° C. for 2 hours, obtaining nanocatalyst.

The nanocatalyst of Comparative Example 3 was evaluated in the same manner as Example 1, wherein the reaction temperature was 130° C. Reaction results were shown in Table 9.

TABLE 9 catalytic performances of nanocatalysts of Example 1 and Comparative Example 3 in the reaction of vapour-phase CO oxidative coupling to oxalate

| | Preparation process | One pass conversion of CO (%) | Selectivity for oxalate (%) | Space-time yield of oxalate $(g \cdot L^{-1} \cdot h^{-1})$ |
|---|---|---|---|---|
| Example 1 | nanometals in situ supporting process of the invention | 41 | 99 | 910 |
| Comparative Example 3 | preparation process disclosed by WO03064037A | 10 | 70 | 155 |

As seen from the data in Table 9, the nanocatalyst obtained employing the preparation process disclosed by WO03064037A is not suitable for vapour-phase CO oxidative coupling to oxalate. The possible reasons are as following.

1. The procedure of the preparation process disclosed by WO03064037A is similar as the procedure of the traditional wet impregnation process, all of which include the steps of immersing, drying, calcinating, and reducing with hydrogen gas. The only improvement is that the metal precursor before impregnation is changed to metal-organic chelating agent. A person skilled in the art knows that, it is very hard to obtain a nanocatalyst with uniform size distribution and controllable exposed crystal facet by a traditional wet impregnation process;

2. The preparation process disclosed by WO03064037A employs hydrogen gas as the reductant. A person skilled in the art knows that, when high temperature reduction with hydrogen gas is employed, the nucleating and growing of the nanocrystals are not controlled; thereby it is very difficult to obtain size and exposed crystal facet controllable nanoparticles. However, the nanometals in situ supporting process of the invention employs low temperature reduction with chemical agent. The reducing speed can be controlled by choosing reductants with different strengths, so as to control the growth speed of nanocrystals, and finally obtain size and exposed crystal facet controllable nanocatalysts;

3. The preparation process disclosed by WO03064037A does not use a stabilizer. When the metal-organic chelating agents are reducing by feeding hydrogen gas, the metal nanoparticles are easily aggregated. However, there is a stabilizer in the nanometals in situ supporting process of the invention, and the function of the stabilizer is for suppressing the aggregation of nanoparticles;

4. The preparation process disclosed by WO03064037A employs glycolic acid as the chelating agent, but the nanometals in situ supporting process of the present invention employs an acids or salt containing a citrate or oxalate ion as the capping agent. The capping agents employed are different, and the guiding functions thereof are also different. The nanocatalysts obtained employing glycolic acid as the chelating agent are active for many hydrogenation and dehydrogenation reactions, but they are not suitable for vapour-phase CO oxidative coupling to oxalate.

The above description is only several examples of the invention, without limiting the invention in any way. Although the invention is disclosed by the preferred examples as above, they are not used for limiting the invention. Various alternations or modifications made by a person skilled in the art utilizing the above disclosed technical contents without departing the scope of the technical solution of the invention are all equivalent embodiments, which belong to the scope of the technical solution of the invention.

The invention claimed is:

1. A preparation process for nanocatalysts with (111) crystal facet exposed, comprising the following steps:
   step a), adding carrier into a mixed solution of active component precursor, reductant, capping agent, and stabilizer;
   step b), in situ supporting the active component nanoparticles onto the carrier under the condition of heating and stirring; and
   step c), washing and drying the sample obtained in step b), to obtain the nanocatalysts with (111) crystal facet exposed,
   wherein,
   the active component precursor is a nitrate compound of gold, palladium or platinum, an acetate compound of gold, palladium or platinum, a halide compound of gold, palladium or platinum, or a combination thereof;
   the reductant comprises one or more compounds selected from the group consisting of sodium borohydride, hydrazine hydrate, ascorbic acid, formaldehyde, formic acid, sodium formate, sodium acetate, citric acid, glucose, and ethylene glycol;
   the capping agent is a compound comprising a citrate ion or an oxalate ion; and
   the stabilizer is selected from an organic polymer comprising polyvinylpyrrolidone or poly(ethylene oxide)-poly(propylene oxide)-poly(ethylene oxide) triblock copolymer, or a long chain alkylammonium salt comprising cetyl trimethyl ammonium bromide or cetyl trimethyl ammonium chloride.

2. The preparation process for nanocatalysts according to claim 1, wherein the carrier is pre-treated by placing the carrier into a solution containing promoter metal salt, mixing uniformly under the presence of ultrasonic wave, removing the solvent, drying at 100-200° C. for 1-20 hours, and calcinating at 200-600° C. for 1-20 hours, said promoter metal salt is one compound or the combination of two or more compounds selected from nitrate, acetate, and halide of iron, cobalt, nickel and copper.

3. The preparation process for nanocatalysts according to claim 1, wherein the amount of the reductant is 1-10 times of that of the active component precursor.

4. The preparation process for nanocatalysts according to claim 1, wherein the amount of the capping agent is 1-10 times of that of the active component precursor.

5. The preparation process for nanocatalysts according to claim 1, wherein the capping agent selectively covers the (111) crystal facet of the active component, to suppress the growth of the (111) crystal facet of the active component, so that the finally synthesized active component nanoparticles have exposed (111) crystal facet.

6. The preparation process for nanocatalysts according to claim 1, wherein the amount of the stabilizer is 1-100 times of that of the active component precursor.

7. The preparation process for nanocatalysts according to claim 1, wherein the stabilizer is used for suppressing the aggregation of nanoparticles.

8. The preparation process for nanocatalysts according to claim 1, wherein the heating temperature in step b) is 50-200° C.

9. The preparation process for nanocatalysts according to claim 1, wherein the heating temperature in step b) is 80-150° C.

10. The preparation process for nanocatalysts according to claim 1, wherein the heating temperature in step b) is 90-110° C.

11. The preparation process for nanocatalysts according to claim 1, wherein the heating time in step b) is 0.1-24 hours.

12. The preparation process for nanocatalysts according to claim 1, wherein the heating time in step b) is 0.5-5 hours.

13. A preparation process for vapour-phase CO oxidative coupling to oxalate using nanocatalysts with (111) crystal facet exposed prepared according to the preparation process of claim 1, comprising:
   passing a feed gas containing CO (20-40%), nitrite (10-30%), and nitrogen gas (30-70%), in volume percentage, through a reactor loaded with nanocatalysts with (111) crystal facet exposed to produce oxalate by vapour-phase oxidative coupling reaction, in the reaction conditions with a space velocity of 500-5000 $h^{-1}$, a temperature of 90-160° C. and a pressure of 0.01-2 MPa.

14. The preparation process for vapour-phase CO oxidative coupling to oxalate according to claim 13, wherein the nitrite is any one of methyl nitrite or ethyl nitrite.

15. The preparation process for vapour-phase CO oxidative coupling to oxalate according to claim 13, wherein the oxalate is any one of dimethyl oxalate or diethyl oxalate.

16. The preparation process for vapour-phase CO oxidative coupling to oxalate according to claim 13, wherein the reactor is any one of a single-tubular fixed bed reactor or a multi-tubular fixed bed reactor.

* * * * *